United States Patent [19]
Yum et al.

[11] Patent Number: 4,938,748
[45] Date of Patent: Jul. 3, 1990

[54] URINARY DRAINAGE CONTAINER COMPRISING EXTERNAL SOURCE OF BIOCIDE

[76] Inventors: Su I. Yum, 1021 Runnymead Ct., Los Altos, Calif. 94021; Felix Theeuwes, 1634 Fallen Leaf La., Los Altos, Calif. 94022

[21] Appl. No.: 239,563
[22] Filed: Sep. 1, 1988
[51] Int. Cl.⁵ .............................................. A61M 1/00
[52] U.S. Cl. .................... 604/323; 604/890.1
[58] Field of Search .................. 604/322–327, 604/265, 890.1; 422/292, 294; 4/144.1–144.3, 144.4

[56] References Cited

U.S. PATENT DOCUMENTS 3,312,221  4/1967  Overment .......................... 604/323
3,468,471  9/1969  Linder ................................. 422/294
4,392,848  7/1983  Lucas et al. ....................... 604/265
4,740,201  4/1988  Theewes ............................. 604/85

FOREIGN PATENT DOCUMENTS

84/04036  10/1984  World Int. Prop. O. .

*Primary Examiner*—J. L. Kruter
*Attorney, Agent, or Firm*—Paul L. Sabatine; Edward L. Mandell; Steven F. Stone

[57] ABSTRACT

A patient-care apparatus comprising a container for receiving a biological fluid, and a delivery device on the outside of the container, which device comprises a biocide that is released to the container for preventing the multiplication of and/or eliminating the presence of unwanted pathogens in the container.

1 Claim, 3 Drawing Sheets

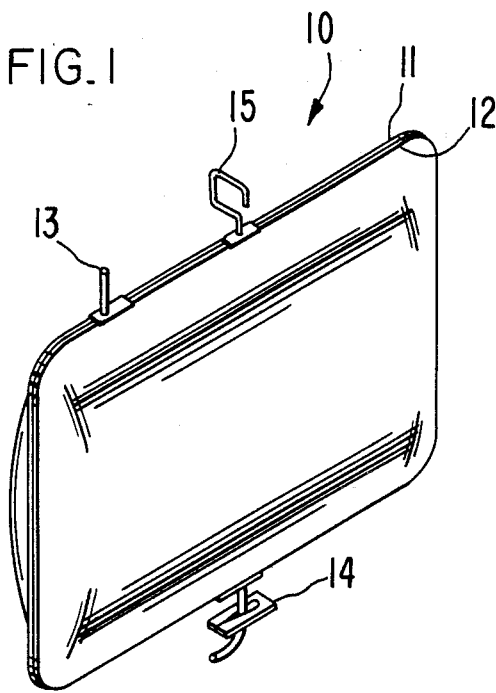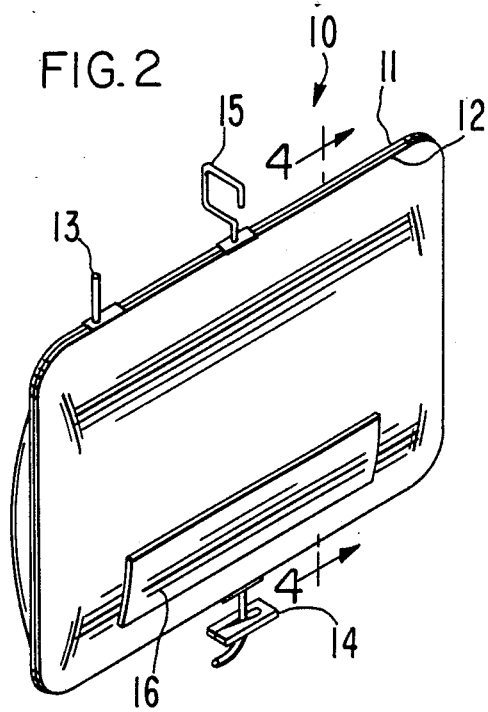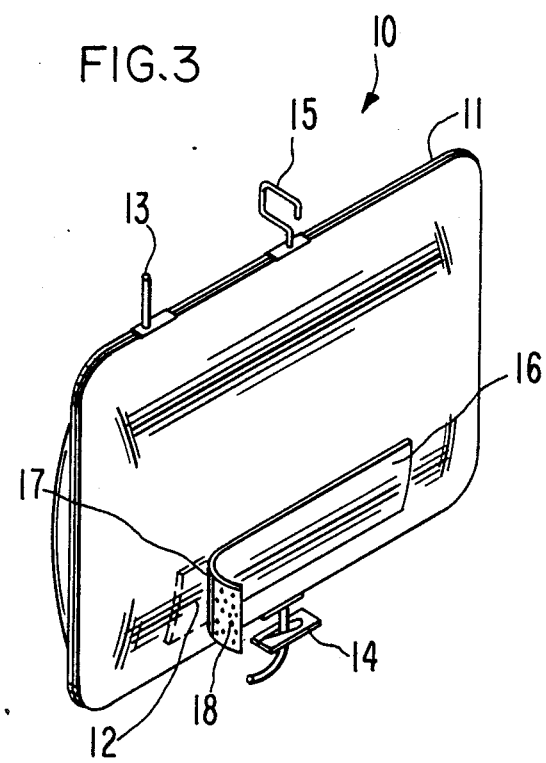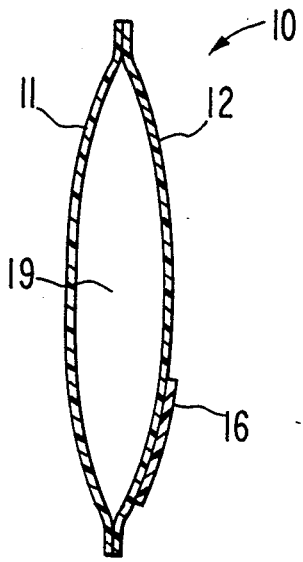

URINARY DRAINAGE CONTAINER COMPRISING EXTERNAL SOURCE OF BIOCIDE

FIELD OF THE INVENTION

This invention pertains to a patient-care apparatus comprising, in combination, a container comprising an external biocidal means releasably positioned on the outside wall of the container for delivering a biocide through the wall into the container. More specifically, the invention relates to an urinary drainage container comprising an external source of biocide. The biocide is delivered into the container for preventing and eliminating the presence of unwanted pathogens present inside the container.

BACKGROUND OF THE INVENTION

It is now generally acknowledged that indwelling catheterization in medical, surgical, gynecological, urological and other patients leads to serious infection of the urogenital tract. The process of indwelling catheterization is performed in approximately 10 to 15 percent of hospitalized patients. Despite the use of the most careful aseptic techniques undertaken while the catheter is in the patient, approximately fifty percent of the patients develop an infection when a catheter is in place for twenty-four hours or longer. This is harmful to the patient because they are subjected to the risk of cystitis, acute pyelonephrititis and life-threatening septicema, which carries a risk of mortality, as reported in *Arch. Internal Med.*, Vol. 110, pp 703–11, (1962); *Antimicrob. Agents Chemother.*, pp 617–23, (1963); and *Lancet.* Vol. 1, pp 310–12, (1960).

The occurrence of the above-mentioned infections is encouraged by many circumstances. These circumstances include prolonged use of indwelling Foley catheters often accompanied by the absence of a sterile insertion and maintenance techniques, and by having the catheter connected to a clean, but not sterile drainage collection container placed in the immediate vicinity of the patient's bed. These and other circumstances that predispose a patient to infection are reported in *Urinary Tract Infection And Its Management,* edited by Kaye, D., Chapter 15, "Care of the Indwelling Catheter," pp 256–66, (1972), published by the C. V. Mosby Company, St. Louis, Mo.; and in "Factors Predisposing To Bacteriuria During Indwelling Urethral Catheterization," *New Eng. J. Med.*, Vol. 291, pp 215–23, (1974).

Attempts have been made to reduce the incidence of catheter acquired infection and to reduce the presence of unwanted organisms in drainage containers, but these attempts have not met with general acceptance. For example, one attempt consists in systemic chemoprophylaxis achieved by orally administering an antibiotic such as chloramphenicol, penicillin or streptomycin. This attempt, however, affords no significant protection against the acquisition of infection after indwelling catheterization, as reported in *Arch. Internal Med.*, Vol. 110, pp 703–11, (1962); *Acta Chiv. Scand.*, Vol. 118, pp 45–52, (1959); and *Dis. Mon.*, pp 1–36, (Sept. 1960).

The attempts for preventing or eliminating unwanted organisms also include adding a biocide to the inside of a drainage container, or placing a device inside the container wherein the device releases a biocide. For example, formalin is added to the fluid collection container for controlling, that is, killing pathogens. This method, however, does not enjoy general use because there is a risk of siphoning formalin into the urinary tract, as reported in *British Med. J.*, Vol. 2, pp 4233–25, (1964). In U.S. Pat. No. 4,233,263 the patentee Shaeffer disclosed adding 3% hydrogen peroxide solution to a urine bag for reducing the risk of urinary tract infection. This method is inherently subjected to poor results because of a lack of compliance. This is, each time urine is drained from the urinary drainage bag the hydrogen peroxide is drained and it must be reintroduced into the bag. This requires mixing and agitation, and it is often accompanied by spilling of the solution. Also, hydrogen peroxide loses its strength over time. In U.S. Pat. Nos. 4,193,403 and 4,241,733 Langston et al discloses a device inside a urinary drainage bag. The device contains paraformaldehyde that depolymerizes to formaldehyde in the presence of moisture inside the drainage bag. While formaldehyde is an antimicrobial, it is not used because it may be injurious to an animal host.

It will be appreciated by those versed in the urinary drainage art that, in view of the above presentation, a critical need exists for a novel and unique means for introducing a biocidal agent into a urinary container. The need exists for overcoming the difficulties associated with the prior art use of an internal biocide and an internal delivery device. It will be further appreciated that a pressing need exists for a means that is not introduced into the container, but can provide a biocidal agent from an external delivery source in contact with the outside of the drainage container.

OBJECTS OF THE INVENTION

Accordingly, it is an immediate object of the invention to provide an improvement in urinary drainage collection, which improvement overcomes the disadvantages associated with the prior art.

It is a further object of the invention to provide a drainage collection system comprising, in combination, a urine receiving container and means for positioning on the exterior of the container for delivering a biocide that enters the container for preventing the multiplication of and/or the elimination of pathogens in the container.

Another object of the invention is to provide a delivery device that is releasably mounted on the exterior of the urine receiving container for delivering a biocidal agent into the container.

Another object of the invention is to provide an urinary drainage container with an external detachable dispensing device that releases an antipathogenic agent, and which detachable dispensing device embraces inventive simplicity, is inexpensive to make, and is disposable.

Another object of the invention is to provide a delivery device for positioning on the external surface of a drainage container, wherein the delivery device comprises a shape that corresponds to the shape of the external surface of the container.

Another object of the invention is to provide a detachable pouch for positioning on the outside wall of an urinary drainage container, and which pouch contains a biocide that passes through the wall into the container for preventing bacterial contamination within the container.

These and other objects of the present invention will become more apparent upon a consideration of the drawings, the specification and the accompanying claims.

BRIEF DESCRIPTION OF THE DRAWINGS

In the drawings, which are not drawn to scale, but are set forth to illustrate various embodiments of the invention, the drawing figures are as follows:

FIG. 1 is a partially exposed view of an urinary collection container used for the purpose of this invention;

FIG. 2 is a side view of an urinary drainage container with a dispensing device releasably attached to the container;

FIG. 3 is a side view of an urinary drainage container depicting a dispensing device in partially opened, peeled-back configuration, positioned on the external surface of the container;

FIG. 4 is an enlarged, fragmentary sectional view of the drainage container delivery device assembly of FIG. 2, taken through 4—4 of FIG. 2;

In the specification and in the drawing figures like parts in related figures are identified by like numbers. The terms appearing earlier in the specification and in the drawing figures, as well as embodiments thereof, are further discussed elsewhere in the disclosure.

DETAILED DESCRIPTION OF THE DRAWINGS

Figure 5:
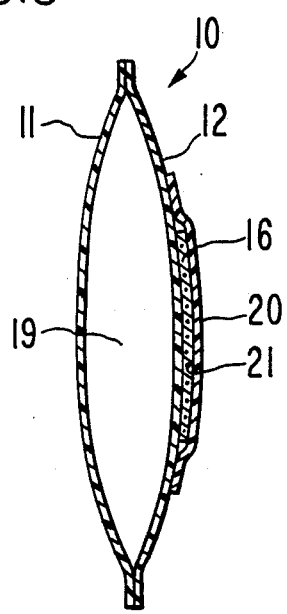
FIG. 5 is an enlarged, fragmentary sectional view of the drainage container delivery device assembly of FIG. 2, taken through 4—4 of FIG. 2, for depicting an external delivery device comprising a backing member and a reservoir releasably positioned on the outside wall of a drainage container.

Turning now to the drawings in detail, which are examples of various embodiments of the invention, and which examples are not to be construed as limiting the invention, one embodiment of an urinary drainage container is indicated in FIG. 1 by the number 10. In FIG. 1, there is illustrated one embodiment of a bedside drainage container 10 designed for use in a closed catheter system. In one preferred manufacture bedside drainage bag 10 is made from two films of polyvinyl chloride plastic 11 and 12. The two films are sealed to each other around their peripheral edges, for example by an electronic welding procedure or heat sealed to each other to provide sealed container 10. Optionally one wall comprising the container may be transparent or translucent for exposing the contents of the container. In a preferred embodiment, the other wall is opaque. The wall is made opaque by the addition of $TiO_2$. Drainage container 10 preferably is manufactured as a bag, and it is provided with an inlet fitting 13 for receiving a catheter for letting fluid flow into the container. Drainage container 10 also is provided with a drainage assembly 14 for periodically draining the contents of the container. A hook 15 is fixed to the top of container 10 for hanging the container on a bedside stand.

In FIG. 1, container 10 is illustrated in an essentially closed or flat state. Container 10, when put into use, generally is free of air at the beginning of receiving fluid from a patient. Over time, as fluid drains into container 10, flexible walls 11 and 12 bulge outward, thereby increasing the space inside the container for receiving an increasing volume of urine.

In another embodiment container 10 may be manufactured as a bag comprising a flexible polymeric composition. Container 10, when made as a bag, can be produced by blowing an extruded tube of the polymeric composition to conform to the interior of a mold cavity having the desired configuration.

In a presently preferred embodiment at least one of wall 11, or wall 12, or both wall 11 and wall 12, is made from a polymeric composition that permits the passage of a biocidal agent from an outside delivery source through wall 11 or wall 12 into the inside of container 10. Representative polymeric composition for forming walls 11 and 12 comprise olefin polymers, vinyl polymers, condensation polymers, addition polymers, rubber polymers and silicon polymers. More specific polymers comprise a member selected from the group consisting of polyethylene, polypropylene, polyvinyl acetate, polyvinyl acetal, polyvinyl chloride, polyamide, polyester, butadiene rubber and organosilicon polymers. Walls 11 and 12 optionally comprise a plasticizer such as a member selected from the group consisting of phthalate ester, adipate ester, sebacate ester, azelate ester, di-2-ethylhexyl phthalate, butyl phthalyl butyl glycolate, diamyl phthalate, dibutyl succinate, diethylene glycol dipropionate, ethylphthalyl, ethylglycolate, tributyl citrate, tributyl phosphate, triethylene glycol dibutyrate, glycol monoleate, polyethylene glycol 200; polyethylene glycol 400-ML, diethyl lauramide, oleic and mineral oil, and the like. The amount of plasticizer in a wall is from 0.01 weight percent (wt %) to 10 wt %, or more.

FIG. 2 illustrates an urinary drainage container 10 comprising a wall 11, a wall 12, an inlet 13, an outlet port 14, a hook 15, and a biocidal delivery device 16 releasably positioned on the outside wall 12 of container 10. Delivery device 16 can be placed at any position on the outside of the container, usually near the bottom. Also, delivery device 16 can be positioned vertically on the outside wall of container 10.

FIG. 3 depicts the urinary drainage container 10 of FIG. 2 comprising wall 11, wall 12, inlet port 13, outlet port 14, hanging hook 15 and biocidal delivery device 16 releasably mounted onto an external surface of wall 12 of container 10. In FIG. 3, delivery device 16 is peeled-open at 17 for illustrating delivery device 16 in biocide 18 delivery position on wall 12. Delivery device 16, in one embodiment, is a reservoir formed of a polymeric composition comprising a biocide agent 18. The polymer composition stores and releases a biocide 18 by diffusion or by osmotic action to wall 12. Representative polymers for forming delivery device 16 comprise a homopolymer, copolymer, cross-linked polymer, diffusion polymer or a microporous polymer. Examples of polymers include acrylic polymers and copolymers of methacrylate, ethylacrylate, ethylmethacrylate, and methylmethacrylate; homopolymers and copolymers including vinylchloride-vinylacetate copolymer; chlorinated vinyl chloride; polyethylene; polypropylene; ethylene-propylene copolymer; chlorinated polyethylene; ethylene-vinyl acetate copolymer; styrene-butadiene copolymer; acrylonitrile-styrene-butadiene terepolymer; polyvinylidene chloride; vinylchloride-acrylonitrile copolymer; vinylchloride-vinylidene chloride copolymer; vinylidenechloride-acrylate ester copolymer; polybutylene terephthalate; vinylchloride-acrylate ester copolymer; cross-linked polyvinyl acetals such as cross-linked polyvinyl formal; cross-linked polyvinyl acetal and cross-linked polyvinyl butyral; polyethers; polyesters; sparingly cross-linked polyesters; polyurethane; polyamide; chlorosulfonated polyolefins; polyolefins; polybutadiene; polyisoprene; polysilicone; and the like. The polymers are known in *The Handbook of Common Polymers*, by Scott et al., (1971), published by CRC Press, Cleveland, Ohio; in *Modern Plastics Encyclopedia*, (1979), published by McGraw-Hill Inc., New York, N.Y.; and in *Handbook of Plastics and Elastomers*, by Harper, (1976), published by McGraw-Hill Inc., San Francisco, Calif.

The biocides useful for the purpose of the invention include a member selected from the group consisting essentially of a phenol, quaternary ammonium biocides, surfactant biocides, chlorine-containing biocides, quinoline, quinaldinium, lactone, antibiotics, dye, thiosemicarbazone, quinone, sulfa, carbamates, urea, salicylamide, carbanilide, amide, guanide, amidine, chelate and imidazoline biocides.

Exemplary biocidal dyes include acridine, acriflavine, aminacrine hydrochloride, proflavin hemisulfate, triphenylmethane, magenta, crystal violet, scarlet red, pararosaniline, and rosaniline. Exemplary chlorine releasing biocides include sodium hypochlorite, oxychlorosene, chloramine, dichlorodimethylhydantoin, halazone, dichloramine, chlorasine, succinchlorimide, trichloroisocyanuric acid, dichloroisocyanurate, trichloromelamine, dichloroglycoluril, halogenated dialkyl-hydantoin, and halane.

Exemplary biocidal quinaldinium and quinoline biocides are dequalinium, laurolinium, hydroxyquinoline, lioquinol, chlorquinaldol and halquinol. Exemplary quaternary ammonium biocides include pyridinium biocides, benzalkonium chloride, cetrimide, benzethonium chloride, cetylpyridinium chloride, chlorphenoctium amsonate, dequalinium acetate, dequalinium chloride, domiphen bromide, laurolinium acetate, methylbenzethonium chloride, myristyl-gamma-picolinium chloride, ortaphonium chloride, and triclobisonium chloride. Exemplary furans include greseofulvin, nitrofurfural, nitrofurazone, nitrofurantoin, furazolidone, and furaltadone.

Exemplary phenol biocides include a member selected from the group consisting essentially of chlorinated phenol, cresol phenol, thymol, chlorocresol, chloroxylenol, hexachlorophane, bisphenols, amylmetacresol, bithionol, chlorothymol, dichloroxylenol, chiorophene, p-chlorophenol, p-phenylphenol, trinitrophenol, dichlorobisphenol, and bromochlorobisphenol. Exemplary antibiotics include penicillins, gentemyctin, aminoglycosides, benzylpenicillin, ampicillin, tetracylines, cephalosporins, neomycin, chloramphenicol, vancomycin, fudicin, rifampicin, cephaloridine, erythromycin, actinomycin, neomycin, polymyxin, colistin, gentamicin, bactriun, carbenicillin and streptomycin. Exemplary lactones include propiolactone. Exemplary urea biocides include noxytiolin, polynoxylen and triclocarbon.

Examples of other biocides useful for the purpose of the invention are chlorhexidine gluconate, chlorhexidine, chlorhexidine acetate, chlorhexidine hydrochloride, dibromopropamide, halogenated diphenylalkanes, cibromsalan, metabromsalan, tribromsalan, carbanilide, salicylanilide, tetrachlorosalicylanilide, trichlorocarbanilide, propamide isethionate, pentamidine, picloxydine, mendalamine, methenamine salts, the acid addition and quarternary, methenamine mandelate, polyoxmethylene esters such as polyoxmethylene diester, polyoxmethylene diacitate, and the like, and mixtures thereof.

The amount of biocide in device 16 generally will be about 0.1% to 80% by weight, with a more preferred amount of 5% to 50% by weight. The device can be manufactured for releasing anti-infective amounts of biocide over a prolonged period from several hours to 30 days or longer, with a more preferred period of 1 to 14 days. The devices of the invention release from 10 ng to 750 mg per hour, or higher. One device can be used at a time, or two or more devices can be used at a time. The devices can be used in succession, and more than one device can be used simultaneously.

The biocides kill, prevent or retard the presence of harmful or unwanted microorganisms inside a urine container. Typical microorganisms include the fungi *Aspergillus niger, Aspergillus flavus, Rhizopus nigricans, Cladosporium herbarium, Epidermophyton floccosum, Trichophyton mentagrophytes, Histoplasma capsulatum,* and the like. The term, "micro-organisms," also includes *Pseudomonas aeruginosa, Escherichia coli, Proteus vulgaris, Staphyloccus aureau Streptococcus faecalis, Klebsiella, Enterobacter aerogenes, Proteus mirabilis,* other gram-negative bacteria and other gram-positive bacteria, mycobactin, and the like. The term also embraces yeast such as *Saccharomyces derevisiae, Canndida Albicans.* and the like. Additionally, spores of micro-organisms, viruses and the like, are within the intent of the invention.

The biocides are disclosed in *Disinfection, Sterilization and Preservation*, by Block, (1977), published by Lea & Febiger, Philadelphia, Pa.; in *Inhibition and Destruction of Microbial Cells*, by Hugo, (1971), published by Academic Press, New York, N.Y.; in *Martindale, The Extra Pharmacopoeia*, edited by Blacow, published by The London Pharmaceutical Press, London; and in U.S. Pat. No. 4,445,889.

Delivery device 16 can be releasably held on the outside wall of a drainage container by an adhesive. Representative adhesives include a mixtures of 2-cyanoacrylate and dimethyl methylenemalonate, monomeric ester of alpha-cyanoacrylic acid, cross-linked copolymer of dimethylaminoethylmethacrylate and an alkyl acrylate, adhesive composition comprising a hydrocolloid gum, polyisobutylene and cross-linked dextran, silicone medical adhesive, mineral oil-polyisobutylene adhesive, and the like. The adhesive optionally can contain a rheological agent that imparts thixotropic characteristics to the adhesive, aids in increasing its cohesiveness and bond strength, imparts slump control, maintains the delivery device on the container, and lets it be easily removed therefrom at the end of the delivery period. The rheological agents useful for this purpose are silicone compounds such as fumed silica.

FIG. 4 is a sectional view through 4—4 of FIG. 2. In FIG. 4, there is illustrated urinary drainage container 10, comprising two walls, wall 11, and wall 12, delivery device 16 positioned on outside of wall 12, for supplying a biocide to the lumen or inside 19, of drainage container 10.

FIG. 5 is a sectional view through 4—4 of FIG. 2. In FIG. 5, there is illustrated urinary drainage container 10 comprising wall 11, wall 12, lumen 19, and delivery device 16. In FIG. 5, delivery device 16 is covered or laminated with a membrane 20 impermeable to the passage of biocide 21 in device 16. The presence of impermeable membrane 20 insures unidirectional passage of biocide 21 through wall 12 into lumen 19. Backing member 20 comprises occlusive, nonoclusive, flexible and non-flexible materials. Examples of materials that can be used for backing member 20 include high density polyethylene, metal foil used alone, such as aluminum, or metal foil laminated to a polymeric substrate for added strength and toughness. In one preferred embodiment backing member 20 is a composite designed for strength and as a barrier for preventing loss of biocide 21. Multilaminated films also can serve as a backing member comprising a lamina of medium density polyethylene in laminar arrangement with a lamina formed of polyethylene terephthalate on which a thin layer of aluminum was vapor deposited. Siliconized polymers, such as siliconized polyalkylene terephthalate also can be used alone, or in a laminate. In an optional embodiment, not shown, external delivery device 16 can comprise a multilaminate, or a form fill and seal delivery system.

Figure 6:
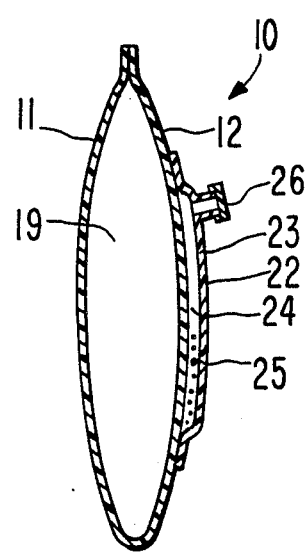
FIG. 6 is an enlarged, fragmentary sectional view of the drainage container delivery device assembly of FIG. 2, taken through 4—4 of FIG. 2, for depicting an external delivery device pouch containing a biocide of a delivery device detachably positioned on an outside surface of the container; and, FIG. 7 and FIG. 8 depict the amount of a biocide that passes through the wall of an urinary container over time.

FIG. 6 is a sectional view through 4—4 of FIG. 2. In FIG. 6, there is seen urinary drainage container 10 comprising a single film comprising with a first wall 11, and a second wall 12, an internal lumen 19 and an external delivery device 22 positioned on the outside of container 10. Delivery device 22 is sized, shaped and adapted as an external pouch. External pouch device 22 comprises a wall 23 that defines an internal space 24 in cooperation with the outer surface of wall 12 of container 10. Wall 23 of pouch device 22 comprises a composition that is substantially impermeable to the passage of a biocide 25 in space 24. The pouch 22 is comprises internally at least in part a biocide 25, or the pouch is filled with biocide 25, which is available for passage through wall 12. Pouch 22 comprises an injection port 26 for filling and refilling reservoir space 24. The biocide 25 can be present in any form that readily makes available biocide 25 to wall 12. Exemplary biocide 25 releasing forms comprise a member selected from the group consisting of solid, crystalline, microcrystalline, particle, pellet, granule, powder, tablet, spray-dried, lyophilized, or compressed forms that release the biocide, such as a compressed powder, compressed granules, and the like. The biocide can be mixed with a carrier such as silicone oil, mineral oil, rapseed oil, palm oil, agaragar, sodium alginate, gum Arabic, methyl cellulose, silica gel, and the like. External pouch 22 can also comprise a biocidal emulsion, a biocidal suspension, an optional permeation enhancer such as glyceryl monoleate, dimethyl sulfoxide, ethanol, and the like, for transporting a biocide through the wall of the container, and the like. The amount of biocide 25 housed in internal space 24 is about 1 milligram to 25 grams, and the like.

Selection of polymers for forming wall 11, or wall 12, for the passage of biocide from the external delivery device, or selection of a polymer for forming an impermeable backing member can be determined by measuring the rate of diffusion through a polymeric material. Various techniques can be used to determine the permeability of a homopolymer, copolymer, or terepolymer to the passage of a biocide. One method that can be used is to position a film of the polymer, of known thickness, as a barrier between a rapidly stirred, saturated solution of the biocide and a rapidly stirred solvent bath, at a constant temperature, typically 25° C., and periodically measuring the concentration in the biocide solution and in the solvent bath. Then, by plotting the biocide concentration in the solvent bath versus time, the absence of the degree of permeability, P, of the polymeric film is determined by Fick's Law of Diffusion. Fick's Law of Diffusion is expressed by the following equation (1):

$$\text{Slope of plot} = (Q_1 - Q_2/t_1 - t_2) = PAC/h$$

wherein
$Q_1$ = cumulative amount of drug in solvent in micrograms at $t_1$
$Q_2$ = cumulative amount of drug in solvent in micrograms at $t_2$
$t_1$ = elapsed time to first sample, i.e., $Q_1$
$t_2$ = elapsed time to second sample, i.e., $Q_2$
A = area of film in cm$^2$
C = concentration of drug in saturated solution
h = thickness of film in cm By determining the slope of the plot, i.e., $[Q_1 - Q_2/t_1 - t_2]$ and solving the equation using the known or measured values of A, C and h, the permeability P constant in cm$^2$/time of the film for a given biocide is readily determined. The procedures used to determine the rate of release through the polymer can be ascertained easily by standard techniques known to the art as recorded in *J. Pharm. Sci.*, Vol. 52, pp 1145–49, (1963); ibid, Vol. 53, pp 798–802, (1964); ibid, Vol. 54, pp 1459–64, (1965); ibid, Vol, 55, pp 840–43 and 1224–39, (1966); *Encyl. Polymer Sci. Technol.*, Vol. 5 and 9, pp 65–82 and 794–807, (1986); the references cited therein, and the like.

Figure 7:
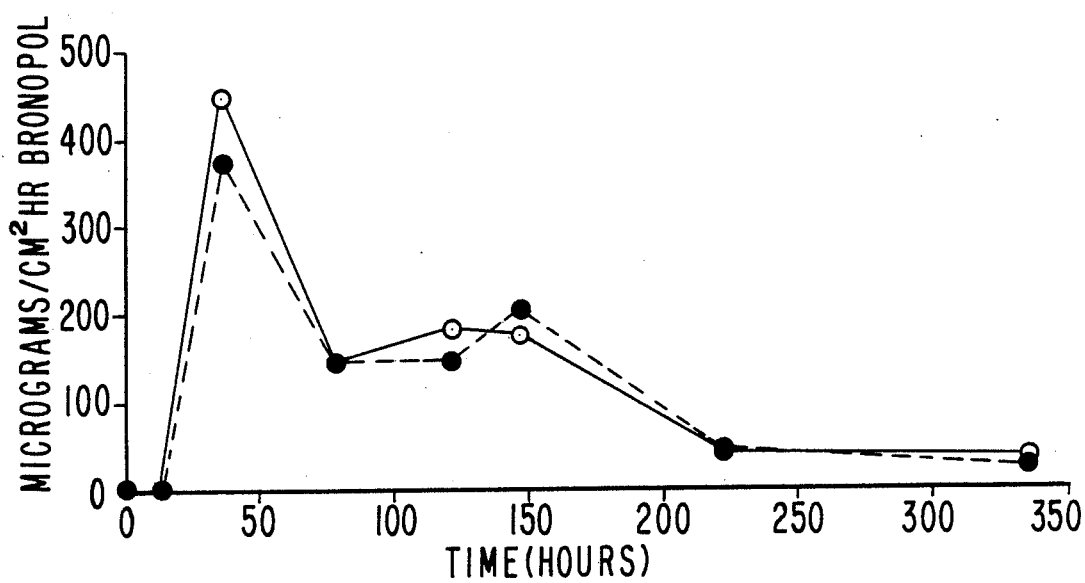
Figure 8:
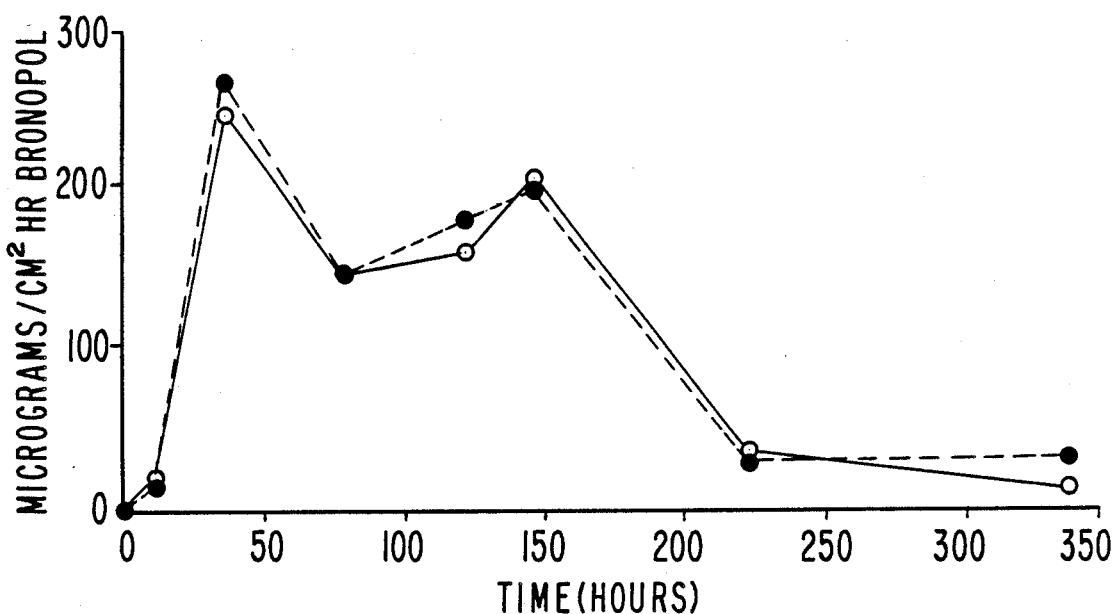

For the purposes of this invention the delivery of the biocide bronopol from an external delivery pouch is seen from the following study: first, 40 mg per ml of bronopol was blended with 5 ml of a biocidal carrier comprising 2.5 ml of tributyl citrate and 2.5 ml of mineral oil and the blend charged into an external, adhesively positioned device on the outside surface of a urinary drainage bag. The bag was made of opaque polyvinyl chloride with a wall thickness of 10 mils, and the bag had an internal lumen of 25 ml. The bronopol delivery rate through the wall of the bag is seen in FIG. 7. In FIG. 7, the clear circle and the darkened circle represent the results of two separate studies. In FIG. 8 the delivery rate of bronopol is depicted through a 9 mil thick opaque or white polyvinyl chloride wall into a bag having a fluid receiving volume of 25 ml. The bronopol was in a carrier as a concentration of 40 mg/ml, which carrier comprised 2.5 ml of tributyl citrate and 2.5 ml of mineral oil, and the area of the wall through which the bronopol passed was 7.07 cm$^2$. The clear circles and the darkened circles represent the results of the two studies.

In a separate experiment, both the minimum inhibitory, MIC, and bactericidal concentrations MBC of bronopol were determined against *E. Coli, P. Aeruginosa, S. Aereus* and *C. Albicans* at 37° C. The initial colony forming unit per test tube ranged from 30 to 450, which was inoculated in the actual human urine whose pH was approximately 6. The MIC values were from 12.5–25 μg/ml, and the MBC ranged from 25–50 μg/ml irrespective of the microorganisms tested.

From this microbiological potency data, average daily urinal output (2000 ml), and the size of a bronopol release system (50–100 cm$^2$), an estimate was made of the required bronopol flux for biocidal control through the walls of urine bag made of poly(vinyl chloride), (PVC). The minimum bactericidal flux presently preferred is about 20–40 µg/cm$^2$hr, which can be accomplished with the bronopol formulation used for the data shown in FIG. 7 and 8. The required, minimum inhibitory flux is approximately 10–20 µg/cm$^2$hr. According to FIGS. 7 and 8, the required bronopol flux was continuously maintained for 7 to 14 days, or longer.

Another device is prepared by casting a film from a solution comprising 20 parts of polyisobutene having a 1,200,000 viscosity average molecular weight; 30 parts of polyisobutene having a 35,000 viscosity average molecular weight; 40 parts of mineral oil and 10 parts of bronopol in chloroform solvent cast onto an biocidal impermeable film of aluminized polyethylene terephthalate. A contact adhesive is applied around the edges of the film comprising the bronopol. The reservoir-backing member is applied to the opaque, outer surface of a urinary drainage bag for delivering the biocide to the inside of the bag over a prolonged period of 18 hours.

It will be understood by those versed in the medical, surgical and patient-care arts that in the light of the present specification, drawings and the accompanying claims, this invention makes available to the art both a novel and useful delivery device and a combination dispensing device and container endowed with beneficial properties. It will be further understood by those versed in the art that many embodiments of this invention can be made without departing from the scope of the invention. Accordingly, it is to be understood the invention is not to be construed as limited, but it embraces all equivalents inherent therein.

We claim:
1. A patient-care apparatus, comprising in combination:
  (a) a container for receiving urine, the container comprising:
    (i) a wall comprising a composition permeable to the passage of a biocide, which wall surrounds;
    (ii) a lumen;
    (iii) an inlet port in the wall for letting urine into the container;
    (iv) an outlet port in the wall for letting urine leave the container:
  (b) a delivery device in communication with the outside of the wall of the container, the device comprising:
    (v) a reservoir comprising a polymeric composition comprising a surface in contact with the composition of the wall of the container permeable to a biocide;
    (vi) about 0.1% to 80% by weight of a biocide in the reservoir, which biocide is delivered at a rate of 10 ng to 750 mg per hour through the wall into the container for substantially preventing and eliminating the presence of pathogens inside the container for a prolonged period of time up to 30 days; and,
    (vii) a backing member in contact with the other surface of the reservoir, the backing member comprising a composition substantially impermeable to the passage of a biocide.

* * * * *